United States Patent
Anders et al.

(10) Patent No.: US 8,701,509 B2
(45) Date of Patent: Apr. 22, 2014

(54) SAMPLING DEVICE

(75) Inventors: Klaus-Dieter Anders, Oberrohrdorf (CH); Dragan Radanovic, Wetzikon (CH)

(73) Assignee: Mettler-Toledo AG, Greifensee (CH)

( * ) Notice: Subject to any disclaimer, the term of this patent is extended or adjusted under 35 U.S.C. 154(b) by 456 days.

(21) Appl. No.: 13/111,631

(22) Filed: May 19, 2011

(65) Prior Publication Data

US 2011/0252898 A1 Oct. 20, 2011

Related U.S. Application Data (63) Continuation of application No. PCT/EP2009/065645, filed on Nov. 23, 2009.

(30) Foreign Application Priority Data

Dec. 3, 2008 (EP) .................................... 08170541

(51) Int. Cl.
*G01N 1/12* (2006.01)
(52) U.S. Cl.
USPC .................. 73/864.63; 73/863.71; 73/864.81; 73/61.48; 73/64.44; 73/64.56; 73/19.06; 73/19.1
(58) Field of Classification Search
USPC ............... 73/863.57, 863.71, 863.72, 863.86, 73/864.33, 864.61, 864.63, 864.64, 23.4, 73/23.41, 23.42, 61.56, 864.83
See application file for complete search history.

(56) References Cited

U.S. PATENT DOCUMENTS

| | | | | |
|---|---|---|---|---|
| 1,621,164 A * | 3/1927 | Hutchings | ..................... | 137/579 |
| 2,736,201 A * | 2/1956 | Ohlsen et al. | ................... | 73/198 |
| 3,948,607 A | 4/1976 | Atwood et al. | | |
| 3,991,055 A | 11/1976 | Godin et al. | | |
| 4,244,919 A | 1/1981 | Chen | | |
| 4,682,507 A * | 7/1987 | Terrell | ...................... | 73/863.57 |
| 4,712,434 A * | 12/1987 | Herwig et al. | ............. | 73/864.63 |
| 4,800,761 A * | 1/1989 | Spencer | ..................... | 73/863.71 |
| 4,811,611 A | 3/1989 | Uffenheimer | | |
| 5,005,432 A * | 4/1991 | Faulkner | .................... | 73/863.86 |
| 5,351,563 A * | 10/1994 | Karpf et al. | ................ | 73/864.84 |
| 5,363,707 A * | 11/1994 | Augenblick et al. | ........ | 73/864.84 |
| 5,384,095 A * | 1/1995 | Golz et al. | .................... | 422/501 |
| 5,945,611 A * | 8/1999 | Welker | ....................... | 73/864.33 |

(Continued)

FOREIGN PATENT DOCUMENTS

DE 4400385 A1 * 7/1995 ............ B01D 53/30
EP 0118964 A1 9/1984

(Continued)

*Primary Examiner* — Hezron E Williams
*Assistant Examiner* — Alexander Mercado
(74) *Attorney, Agent, or Firm* — Standley Law Group LLP (57) ABSTRACT

A sampling device allows samples to be taken from a fluid that is pressurized and/or contains volatile components. The sampling device has a sampling housing (121, 521), an inlet (10, 110, 510), an outlet (11, 111, 511), a measuring cell (17, 317, 517) and a valve unit (118, 534). The valve unit has a valve which, in a first position, connects the inlet to the outlet by way of the measuring cell. In a second position, the valve connects the inlet directly to the outlet, while also disconnecting the measuring cell from both the inlet and the outlet. The valve unit also has at least one adjustable flow restrictor, through which the flow of the fluid through the sampling device is regulated.

18 Claims, 7 Drawing Sheets

(56) References Cited

U.S. PATENT DOCUMENTS

| | | | |
|---|---|---|---|
| 6,142,024 A * | 11/2000 | Rauleder et al. | 73/864.63 |
| 6,576,193 B1 * | 6/2003 | Cui et al. | 422/417 |
| 6,874,351 B2 | 4/2005 | Bloder et al. | |
| 7,008,793 B2 * | 3/2006 | Duriez et al. | 436/29 |
| 7,335,339 B2 | 2/2008 | Berndtsson | |
| 7,401,498 B2 * | 7/2008 | Syage et al. | 73/28.01 |
| 8,109,157 B2 * | 2/2012 | Kanayama et al. | 73/863.72 |
| 8,141,440 B2 * | 3/2012 | Gammon et al. | 73/864.63 |
| 2002/0170364 A1 * | 11/2002 | Gerard et al. | 73/863.86 |
| 2002/0178785 A1 * | 12/2002 | Lo et al. | 73/23.41 |
| 2004/0099068 A1 * | 5/2004 | Welker | 73/863.71 |
| 2005/0066711 A1 * | 3/2005 | Discenzo | 73/64.56 |
| 2006/0263246 A1 | 11/2006 | Berndtsson | |
| 2007/0144274 A1 * | 6/2007 | Gibson et al. | 73/863.02 |
| 2012/0291568 A1 * | 11/2012 | Gransaether | 73/864.63 |

FOREIGN PATENT DOCUMENTS

| | | | | |
|---|---|---|---|---|
| EP | 0508749 A2 | | 10/1992 | |
| JP | 55006208 A | * | 1/1980 | G01N 1/10 |
| JP | 59212735 A | * | 12/1984 | G01N 1/10 |
| WO | 2006/089389 A1 | | 8/2006 | |

* cited by examiner

SAMPLING DEVICE

CROSS-REFERENCE TO RELATED APPLICATIONS

This application is a continuation of, and is entitled to benefit of a right of priority under 35 USC §120 from PCT/EP2009/065645, filed 23 Nov. 2009, which is in turn entitled to the benefit if a right of priority under 35 USC 119 from European application 08170541.0, filed 3 Dec. 2008. The content of each of these applications is incorporated by reference as if fully recited herein.

TECHNICAL FIELD

The invention concerns a sampling device and a method for taking samples from a fluid that is pressurized and/or contains volatile components. The invention also concerns an analytical instrument comprising such a sampling device which is operable to determine at least one chemical and/or physical parameter of the sample under the conditions that already exist in the fluid.

BACKGROUND

The taking of samples from fluids that are pressurized and/or contain volatile components, i.e. liquids or gases, is performed in a variety of fields including, for example, the chemical, biochemical, pharmaceutical, and in particular the food industry. In the food industry, for example, the chemical and physical parameters of gas-containing beverages such as beer or soft drinks are being determined. Such parameters are particularly difficult to measure in beer, since the latter has a strong tendency to foam even with only a slight and/or momentary loss of pressure. The parameter of interest can for example be the content of dissolved gases such as for example oxygen, ozone, nitrogen, carbon dioxide and carbon monoxide, or in the case of beer the $CO_2$ content and/or the oxygen content of $CO_2$-containing beverages.

Until now, such determinations have been and are being performed mostly on samples that are taken out of a production line and then at least partially depressurized under controlled conditions, so that a state of equilibrium will establish itself between the gas that is still in solution and the gas that has escaped from the fluid. From a measurement of the equilibrium pressure and the temperature one can, in turn, deduce the gas content in the fluid using known physical laws. Besides the gas content, other parameters of the sample can also be determined with suitable additional sensors. Such parameters include for example the turbidity, the color, and the content of further components. The measurement of dissolved gas by means of such expansion methods as well as analytical instruments suitable to perform such methods are disclosed in DE 102 13 076 A1 and DE 44 00 385 A1, among other publications.

A related approach is taken in EP 0 118 964 A1 wherein the sample, after it has been injected into a chamber connected to the production line, is pressed by a piston into a measurement cavity in which an equilibrium pressure can then establish itself between dissolved and free gas as described above.

Another possible solution presents itself in the form of a measurement chamber which is separated from the fluid by a selectively gas permeable membrane. The dissolved gas can diffuse through the membrane into the chamber, where it can be measured by means of conventional sensors.

These methods and instruments provide an indirect measurement of the gas content. The taking of a representative sample from a substantially gas-saturated, pressurized fluid in order to measure a volatile component is not possible without adulterating or changing the sample through outgassing. Furthermore, some of the instruments consist of several chambers and measurement chambers and can therefore not be cleaned without a major effort. However, ease of cleaning is a decisive factor particularly for applications in the food industry.

Instruments for the so-called "near-line" or "at-line" measurement of dissolved gases are distributed by the Mettler-Toledo organization under the trade names "InTap 4000" and "InTap 4004". They consist of a transmitter, a sensor and a measuring cell which can be connected to the production line through a valve, so that the measurement can be performed in flow-through mode. Arranged downstream of the outlet of the measuring cell is a fixed-aperture flow restrictor which regulates the flow of the fluid through the measuring cell, so that the fluid is not being depressurized already in the measuring cell. The fluid is depressurized after it has passed through the flow restrictor, i.e. after the measurement.

These instruments allow the measurement of certain parameters under the conditions existing in the production line. However, they are likewise complex in their design and have to be laboriously disassembled for cleaning. It has further been found that sediments from the fluid will accumulate on the flow restrictor, obstructing the latter and thereby corrupting the measurements.

Thus, the object of the present application is to develop an improved sampling device which is of compact design, simple to operate and easy to clean, and an analytical instrument comprising the inventive sampling device, as well as a method for taking samples.

SUMMARY

A sampling device as disclosed herein, for taking samples from a fluid that is pressurized and/or contains volatile components comprises a sampling housing, an inlet, an outlet, a measuring cell and a valve unit with a valve. In a first position of the valve, the inlet is connected by way of the measuring cell to the outlet, and in a second position of the valve, the inlet is connected directly to the outlet, with the measuring cell being bypassed in the second position. The valve unit comprises at least one adjustable flow restrictor whereby flow of the fluid through the sampling device is regulated.

The flow restrictor is arranged in the valve unit, whereby a particularly compact sampling device can be realized which allows the taking of representative samples even from a gas-saturated, pressurized fluid without the sample being corrupted by outgassing prior to the measurement. The adjustable flow restrictor allows the sample to be moved through the measuring cell at a prescribed flow rate. The flow restrictor is preferably arranged between the measuring cell and the outlet. Of course, this same flow restrictor or an additional flow restrictor can also be arranged between the measuring cell and the inlet.

With the valve set at its second position, the measuring cell can be separated from the inlet and the outlet. This opens the possibility to pre-condition the measuring cell in the laboratory, meaning for example that the measuring cell can be set for a certain target range of values. Also in the second valve position, the valve, and thus the inlet and outlet of the measuring cell, can be flushed out with the fluid under investigation or with a cleaning solution without thereby changing the conditioning of the measuring cell. Only after the valve has been set into the first position is the fluid under investigation directed through the measuring cell. The valve unit is designed to be substantially free of dead spaces, so that the risks of contaminating the measuring cell as well as unintentionally admitting air bubbles into the measuring cell are strongly reduced.

The sampling device can be used for taking samples from liquids as well as gases, collectively referred to herein as fluids.

The inlet and/or the outlet can be configured for example as hose adapters and can be connected through a hose or pipe conduit to a container filled with a fluid or to a suitable waste container.

The valve has a substantially cylindrical valve body which is held in a valve seat. The valve body can be turned in the valve seat about its longitudinal axis by means of a first actuator element. The first actuator element can be operated manually by the user, or automatically by means of a suitable controller.

The valve body has a first and a second bore channel to connect the inlet or the outlet to the measuring cell, and a short-circuit channel for the direct connection of the inlet to the outlet. The short-circuit channel and the bore channels are arranged in such a way in the valve body that they cannot communicate with each other. The short-circuit channel or the bore channels are preferably offset from the axis of rotation of the valve body. The short-circuit channel can be parallel to the axis of rotation, and the first and/or second bore channel can be arranged so that they intersect the axis of rotation of the valve body. In a preferred embodiment, the first and/or second bore channel runs at a right angle to the axis of rotation of the valve body. The longitudinal axes of the two bore channels can also be oriented parallel to each other or at an angle to each other. Of course, the bore channels can also be oriented at another angle relative to the axis of rotation of the valve body. Based on this design concept, a very compact valve unit can be built which is particularly easy to operate.

In a further embodiment, the valve body, the flow restrictor, the inlet and the outlet are arranged in the sampling housing. Also arranged in the sampling housing are the measuring cell, the valve seat, as well as a first and a second connector channel which are connected to the measuring cell. The first and second connector channels are preferably closed off at least at one end with a removable closure means, so that these channels will be easy to flush out or to clean mechanically. Preferably, the sampling device can be dismantled as much as possible for cleaning.

In a preferred embodiment, the first and/or the second bore channel in the valve body can have a smaller diameter than the first or second connector channel or inlet connecting to the bore channel, so that the bore channel by itself can function as an additional fixed flow restrictor.

The adjustable flow restrictor can be adjusted continuously or in prescribed increments, so that the flow through the measuring cell can be adjusted to the conditions existing in the fluid.

The term "flow restrictor" is used herein in the sense of an aperture-restricting means and can be designed with different configurations. The use of an adjustable flow restrictor is particularly advantageous if the sampling device is to be used at different locations in a production line where different conditions exist, or if it is to be used in different production lines. An adjustable or variable flow restrictor in the sense of this application is a means that allows the setting of different aperture cross-sections or, more specifically, different sizes of the cross-sectional area of the aperture.

One embodiment of the adjustable flow restrictor is represented by a slider with a passage opening. The slider is arranged at least partially in the valve unit, in particular in the valve body, so that the slider can be moved along the axis of rotation of the valve unit, thereby changing the passage aperture. The range of overlap between the passage opening and the first and/or second bore channel corresponding with the passage opening can be varied, whereby the passage aperture becomes adjustable. By moving the slider, the passage opening is moved relative to the valve bore. The shape and size of the passage opening are essentially matched to the corresponding bore in the valve body. Depending on the position of the slider in the valve body, the flow restrictor can be opened or closed. The axial movement of the slider is controlled by a second actuator which can be set at a fixed position, whereby the flow restrictor passage can be set to a fixed aperture.

The adjustable flow restrictor, in particular in the configuration of a slider, can work together with an elastic element which is arranged inside the valve body, adjacent to that end of the slider which is located inside the valve body. When the slider is pushed axially into the valve body, the elastic element is compressed and the passage opening of the shutter is set free until it is opened to its maximum aperture. As soon as the force on the elastic element is relaxed, the elastic element expands and bears against the slider which, by the restoring force of the elastic element, is reset to its previously set position.

The cooperation between the slider and the elastic element allows the flow restrictor aperture to be opened for a short time interval without loss of the preset position. As the flow restrictor is preferably opened to its maximum aperture, contaminants such as sediments and particles that have accumulated on the flow restrictor and in the measuring cell, as well as bubbles in the measuring cell, can be flushed out of the sampling device by the stream of fluid and can thus be removed easily. The proper functioning of the flow restrictor and the measuring cell can be ensured, and clogging of the flow restrictor can be prevented.

In a further embodiment, the valve body and the adjustable flow restrictor form an integral valve unit, wherein the flow restrictor aperture can be set as a function of the angle of rotation of the valve body. This concept is based on the fact that when the valve body is turned about its longitudinal axis and between its first and second positions relative to the sampling housing, at least one aperture cross-section of a bore channel will be partially closed off by the wall of the valve seat that is formed in the sampling housing.

The adjustable flow restrictor can thus be realized by offsetting at least one central longitudinal axis of a bore channel in the valve body under a controlled angle relative to the central lengthwise axes of the openings formed in the valve seat adjacent to the bore channels and leading to the inlet and outlet or to the connector channels to the measuring cell, whereby a restriction of the aperture cross-section is created.

The integral valve unit allows a sampling device to be realized which is particularly compact and easy to use as it does not need a separate flow restrictor.

In a preferred embodiment, the central longitudinal axes of the first and second bore channels in the valve body are oriented at an angle to each other, so that when the valve unit is set at the first position, only the second bore channel between the second connector channel and the outlet causes a restriction of the aperture cross-section, while the first bore channel allows a maximum flow stream to move between the inlet and the first connector channel.

The valve unit can also function as a further fixed flow restrictor if the first and/or the second bore channel in the valve body are designed with a smaller diameter than the respective adjoining openings.

For special ease of operation, the sampling device has a first and a second limit stop for the first actuator element, delimiting the range of rotation of the valve unit and thus of the valve body.

The flow restrictor of the integral valve unit can be adjusted either by using a valve body with different-sized first and/or second bore channels, or by varying the angle of rotation.

In a further embodiment, the valve unit has a second actuator element serving to adjust and/or secure the adjustable flow restrictor. Using the second actuator element, the valve body can be secured in a fixed position relative to the first actuator element. The integral valve unit can for example have two separate axes, with the first actuator acting on one, and the second actuator on the other, of the separate axes of the valve unit. Furthermore, the range of adjustment of the flow restrictor can be selectively set by varying the distance between the two end stops. Also, as another possibility, end stops that have a fixed distance from each other can be designed to turn together about the central longitudinal axis of the valve body and to function as the second actuator element, which can be secured in a fixed position.

The size of the base area of the measuring cell is determined, among other factors, by a sensor that works together with the measuring cell. In order for the fluid flow and flow rate of the sample to be substantially equal in the measuring cell and the first and second connector channels when the valve is in the first position, the cross-sectional area of the flow stream in the measuring cell should be essentially the same as in the first and second connector channels. This is achieved if the measuring cell has an enlarged diameter in comparison to the connector channels. In other words, the measuring cell has an enlarged base area. In order to maintain the same volume flow to be maintained regardless of the enlarged base area, the measuring cell has in addition a smaller cross-section than the adjoining connector channels.

The measuring cell can be closed with a closure element, with the sensor and/or with a suitable measuring window, which makes the measuring cell easily accessible for cleaning.

At least one wall of the measuring cell can have an inward-projecting contour shape which is formed in the wall, a wall element or the closure element. This contour feature allows the geometry of the measuring cell to be adapted, so that the conditions regarding the flow stream cross-section can be met and the measuring cell will have a flow stream cross-section essentially equal to or smaller than the connector channels connected to the measuring cell. The contour feature can also serve the purpose of adapting the geometry of the measuring cell and thus its flow stream cross-section to a surface contour of the sensor that projects into the measuring cell. The contour feature in the wall of the measuring cell can be shaped in different ways.

Particularly preferred is an essentially transparent design of the sampling device, so that for example contaminations of the device can be detected optically and/or visually. This detection can occur either through the user's own eyes and/or with a suitable optical detection unit.

A sampling device as disclosed herein can be used in particular with an analytical instrument for the determination of a chemical and/or physical parameter of a sample of a fluid that is pressurized and/or contains volatile components. The analytical instrument can have an analysis housing. Arranged in the analysis housing are a sensor that works together with the measuring cell of the sampling device, and also a transmitter. The transmitter can be configured as part of a processor unit.

Preferably, the sampling device is releasably connected to the analysis housing. This allows an exchange of the sampling device in the analytical instrument, so that for example different fluids can be measured sequentially with the same analytical instrument. Furthermore, one or more sampling devices and/or analytical instruments can be incorporated in a process system. For example, a sampling device can be incorporated in a system as a fixed component to which an analysis housing can be connected in case measurements need to be performed.

As the sampling device can be preconditioned for a target range of values, the analytical instrument is distinguished by particularly fast response times, which is particularly advantageous in measurements of low concentrations of volatile components of the fluid. A sampling device with the capability of being preconditioned preferably comprises a tightly enclosed measuring cell. The measuring cell can be closed off against the outside for example by a closure element, a measurement window, or a part of the sensor.

A plurality of sampling devices that are preconditioned for different fluids or different ranges of target values can thus be prepared and kept ready for their subsequent use. Besides different target value ranges, it is also possible that dry sampling devices or sampling devices already loaded with a fluid are held ready, so that through an exchange of sampling devices different fluids can be measured sequentially with an analytical instrument. In this way, one can for example avoid the risk that measuring results may be falsified by residues of previously measured fluids.

An analytical instrument as disclosed herein can be used for mobile as well as stationary applications. For use in a mobile situation, it is advantageous if the analytical instrument has a mains-independent power source and is designed for portability.

For the sensor for an analytical instrument as disclosed herein, a suitable choice would be for example an optical, amperometric, potentiometric, electrochemical or opto-electric sensor, preferably arranged as an exchangeable unit in the analysis housing and/or in the sampling device.

Besides flow-though measurements, the measuring cell can also be used to perform measurements on stationary samples which are brought into the measuring cell in the flow-through mode, i.e. with the valve in the first position, and which are subsequently locked into the measuring cell by switching the valve into the second position.

To perform the process of taking a sample, the valve is initially in the second position and the inlet of the sampling device is connected to a container which holds the fluid that is to be investigated. Now the fluid can flow through the inlet and the short-circuit channel directly to the outlet, whereby the conduit from the container to the inlet as well as the inlet, the short-circuit channel and the outlet are rinsed by the fluid. Among other things, the rinsing has the effect of outgassing the conduit from the container independently of the measuring cell, without influencing for example the preconditioning of the measuring cell. The flow restrictor can be set by means of the second actuator element. Next, the valve unit is turned into the first position by means of the first actuator element. Depending on the configuration, the at least one flow restrictor is opened for a short time interval to its maximum aperture already during the turning movement. When the valve is in the first position, the fluid streams from the inlet through the measuring cell to the outlet, passing along the way through the two bore channels in the valve body. Due to the preset flow restrictor, the fluid can now be measured by the sensor of the analytical instrument in the measuring cell in a defined flow-through stream in which the conditions prevailing in the fluid container, for example the saturation pressure, are being maintained.

This configuration has the particular advantage that it makes the sampling device easy to clean, even with aggressive commercial cleaning agents and methods, and that it has a valve unit that is essentially free of dead spaces. With its rinsing function, the valve unit further offers a simple way of removing sediments, bubbles and similar unwanted particles from the sampling device during operation. This can be performed for example prior to every measurement. A sampling device as disclosed herein can also be used for taking samples under sterile conditions.

Obviously, a valve as disclosed herein with an adjustable flow restrictor can also be used in other devices and instruments.

BRIEF DESCRIPTION OF THE DRAWINGS

Different embodiments of the sampling device and of the analytical instrument are described in more detail by referring to the attached drawings, wherein.

DETAILED DESCRIPTION

Figure 1:
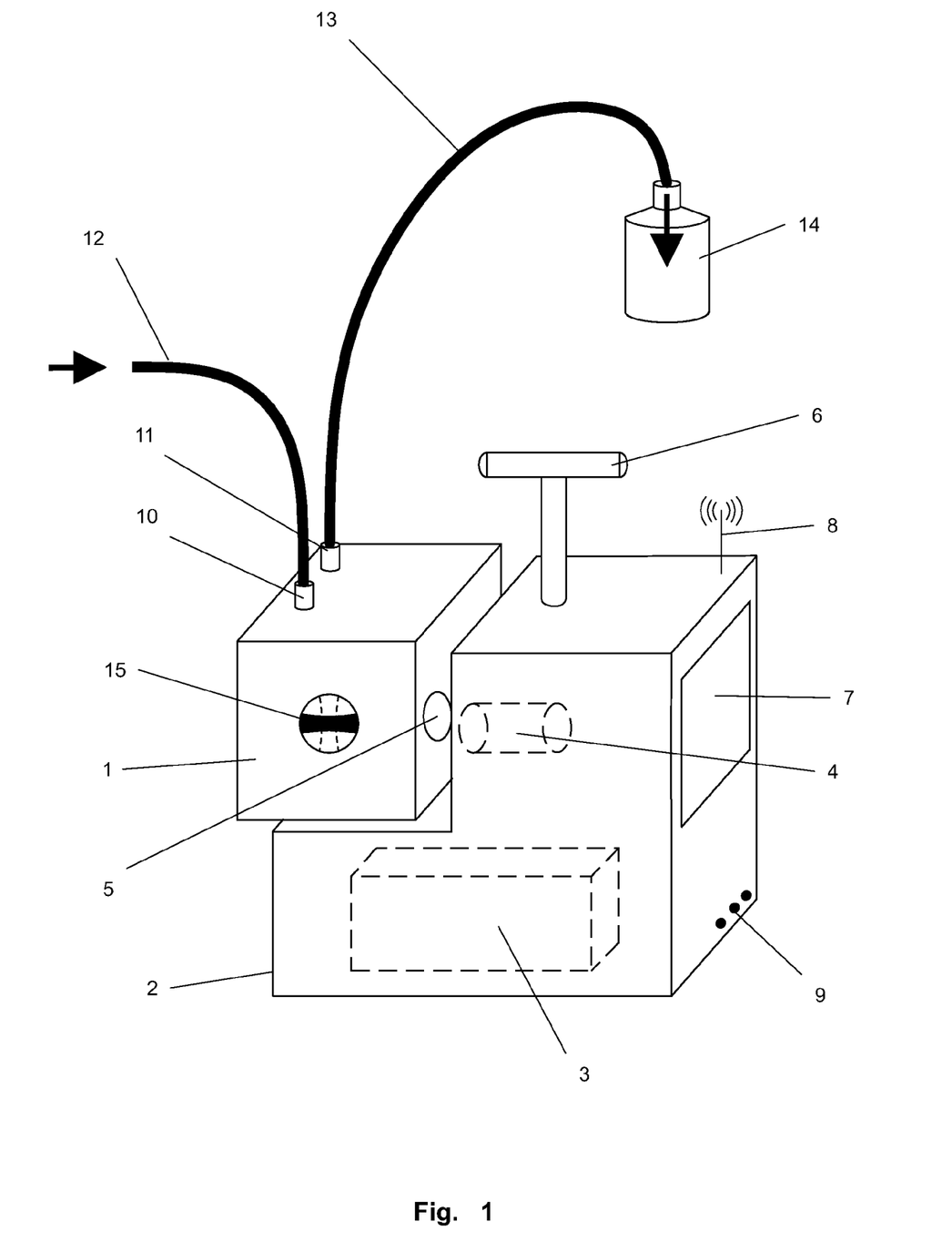
FIG. 1 is a simplified schematic illustration of an analytical instrument with an exchangeable sampling device.

In a simplified schematic view, FIG. 1 illustrates an embodiment of an analytical instrument with a sampling device 1. The analytical instrument comprises an analysis housing 2, to which the sampling device 1 can be releasably connected. The sampling device 1 and the analysis housing 2 can thus be completely separated from each other. The sampling device 1 can be uncoupled from the analytical instrument and exchanged, for example against another, a preconditioned or a cleaned device. The analysis housing 2 can likewise be connected to different sampling devices 1, if the latter are for example permanently installed in a process system. The sampling device 1 and/or the analysis housing 2 can carry a unique marking for their identification.

As shown here in a simplified, schematic manner, the analysis housing 2 contains a transmitter 3, which can be part of a processor unit that is likewise arranged in the analysis housing, and an exchangeable sensor 4. The sensor 4 is arranged in the analysis housing 2 in a manner that allows the sensor to work together with a measuring cell that is arranged in the sampling device 1 and indicated here by a connector port 5 in the sampling device 1, so as to enable the sensor to take measurements on a sample in the measuring cell.

The sensor 4 can for example be an optical, amperometric, potentiometric, electro-optical, or electrochemical sensor. The analytical instrument has the capabilities to measure stationary samples that are enclosed in the measuring cell as well as samples in a state of flow through the measuring cell.

The analytical instrument shown in FIG. 1 is configured as a portable instrument with a carrying handle 6 for transportation. Depending on the design, the indicator panel 7 serves to display the output of measurement values and/or to enter measurement parameters, control commands and sample information. Of course, the analytical instrument can also be remote-controlled, for example by exchanging signals through a wired connection and/or in a wireless mode between a unit that is not shown in the drawing, for example a computer, and the analytical instrument. The analytical instrument is equipped for this purpose with a suitable transmitter/receiver unit 8 and/or suitable connector terminals 9. Such elements 8 and 9 are commonly known and do not need to be explained. The transmitter/receiver unit 8 and connector terminals 9 can also be used for the transfer of data and measurement results. In a further embodiment that is not illustrated here, the sensor is arranged in essence inside the sampling device and/or the analysis housing.

Besides the connector port 5 to the measuring cell, the sampling device 1 has an inlet 10 and an outlet 11. The inlet 10 can be connected by way of a conduit 12, for example a hose or a pipe connection, to a vessel (not shown in the drawing) such as for example a pipeline, a process system or a container that holds the fluid to be analyzed. The outlet 11 can be connected through a further conduit 13 to a suitable waste container 14 as shown here by way of example.

Also shown in FIG. 1 is a first actuator element 15, whereby a valve unit that is arranged in the sampling device 1 can be moved between at least two different positions.

Different configurations and details of a sampling device 1 are explained more extensively through the FIGS. 2 to 17.

Figure 2:
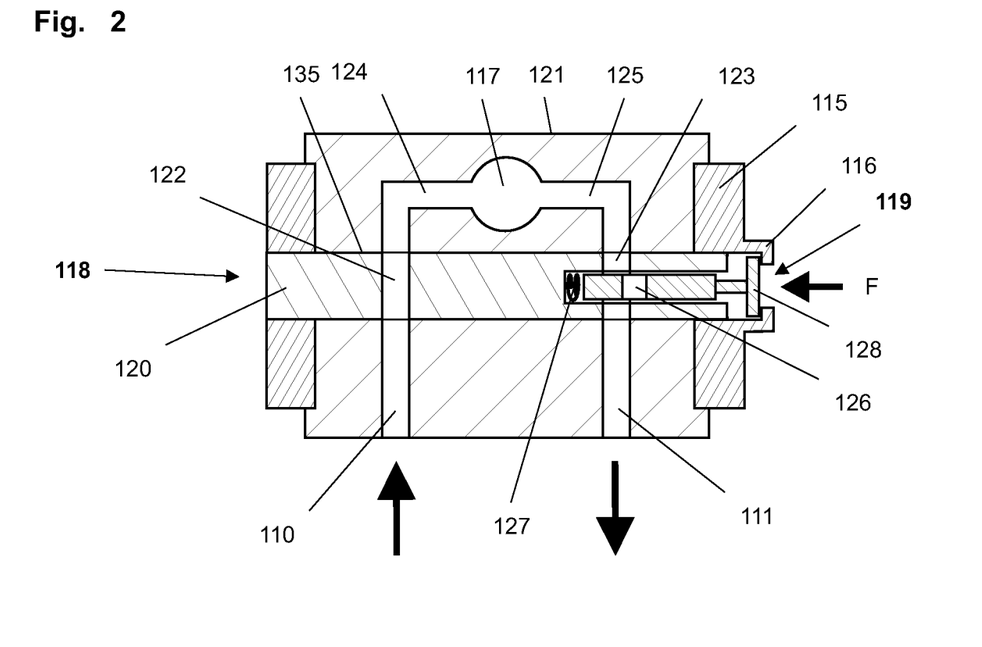
FIG. 2 is a simplified schematic illustration of a sampling device with an adjustable flow restrictor in a sectional view, wherein the valve is set to a first position.

FIG. 2, in a sectional view, shows a schematic representation of a first embodiment of the sampling device. The sampling device has an inlet 110, an outlet 111, a measuring cell 117 and a valve unit 118 with a flow restrictor that is formed in a slider 119.

The terms "inlet" and "outlet" as used herein are meant to refer not only to the outside openings of the sampling device, but also to the conduit channels directly connected with these openings.

The valve unit 118 consists in essence of a cylindrical valve body 120 which is connected at least at one end or, as shown here, at both ends to a first actuator element 115. The valve body 120 is seated, with the freedom to turn about its longitudinal axis, in a valve seat 135 which is formed in the housing 121 of the sampling device. By operating the actuator element 115, the valve unit 118 can be moved from the first position shown in FIG. 2 to the second position shown in FIG. 3.

In FIG. 2, where the valve unit 118 is shown in the first position, the first and second bore channels 122, 123 can be seen which are formed in the valve body 120. In this position of the valve unit 118, the first bore channel 122 connects the inlet 110 by way of a first connector channel 124 to the measuring cell 117, and the second bore channel 123 connects the measuring cell to the outlet 111 by way of a second connector channel 125, so that a stream of fluid can move through the measuring cell 117.

Figure 3:
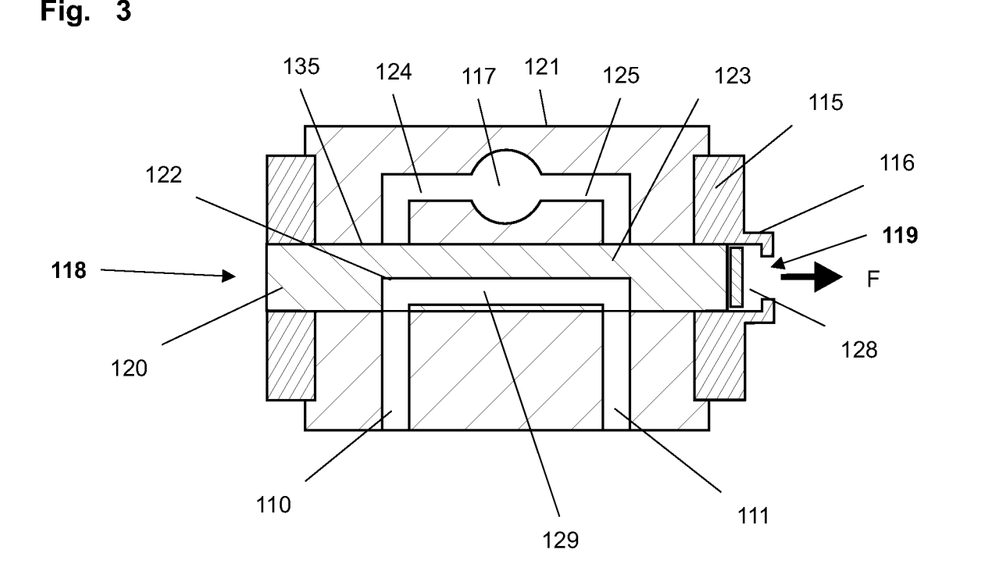
FIG. 3 is a simplified schematic illustration of the FIG. 2 sampling device in a sectional view, wherein the valve is set to a second position.

The slider 119 has a passage opening 126 which restricts the aperture cross-section of the bore channel 123 to a greater or lesser extent as the slider 119 is moved by means of a second actuator element 128 along the lengthwise axis of the valve body 120. The cross-section that is being restricted by the passage opening 126 represents the flow restrictor. The fluid flow through the sampling device can be varied by changing the depth to which the slider 119 is inserted into the valve body 120 (also see FIGS. 4 and 5). The setting of the flow restrictor can be adjusted and secured with the second actuator element 128. FIGS. 2 and 3 show only one slider 119. Of course, the slider 119 could also be arranged at the other end of the valve body 120, or the sampling device could have two sliders.

Also arranged inside the valve body 120 is an elastic element 127 which bears against the end of the slider 119 that faces towards the interior of the valve body 120. By applying a force F to the second actuator element 128 at the other end of the slider 119, for example by pushing against the element 128, the elastic element 127 is being compressed and the flow restrictor is opened. As soon as the pushing force F against the elastic element 127 is relaxed, the restoring force of the elastic element 127 returns the slider 119 to its previous position, whereby the preset shutter aperture is reestablished. In this way, the flow stream through the sampling device can be maximized during a short time interval, so that for example sediments accumulated on the flow restrictor and/or bubbles in the measuring cell can be removed quickly and easily. The range of movement of the slider 119 along the longitudinal axis of the valve body 120 is delimited at one end by the bottom of the recess in the valve body 120 and at the other end by an end stop 116.

FIG. 3 shows the valve unit 118 in the second position. In this position of the valve, the inlet 110 and the outlet 111 are directly connected to each other through a short-circuit channel 129 which runs inside the valve body 120, parallel to the longitudinal axis of the latter. The measuring cell 117 is separated from the inlet 110 and the outlet 111.

The short-circuit channel 129 and the bore channels 122, 123 are formed in the valve body 120 in such a way that they do not communicate with each other. This can be accomplished through a design where the bore passages 122, 123 or the short-circuit channel 129 are offset from the central longitudinal axis of the valve body 120. The bore channels 122, 123 can be oriented either parallel or at an angle to each other. It is also conceivable that at least one of the bore channels 122, 123 has an angular direction change within itself.

Figure 4:
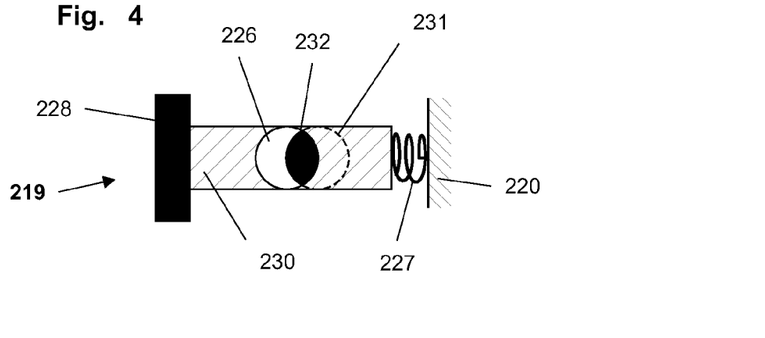
FIG. 4 is a schematic sectional view of the slider in a first position.
Figure 5:
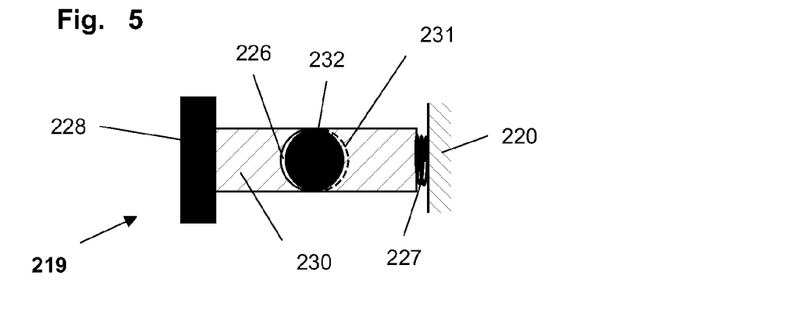
FIG. 5 is a schematic sectional view of the FIG. 4 slider in a second position.

A slider 219 which is configured as a flow restrictor and its function are illustrated schematically in FIGS. 4 and 5. The slider 219 consists of a second actuator element 228 which is connected to an insert 230. A substantially circular opening 226 is formed in the insert 230. The cross-section of the opening 226 essentially matches the cross-section of the connector channel 125.

FIG. 4 shows the slider 219 partially pulled out of the valve body 220. The valve body 220 is only symbolically indicated. In the illustrated position, the opening 226 is offset from the cross-section of the bore channel 231 and thus restricts or reduces the passage cross-section, so that a fluid can move only through the reduced cross-section 232 shown in black in FIG. 4, which is smaller than the cross-section of the bore channel 231.

FIG. 5 shows the slider 219 pushed almost completely into the valve body 220, so that the opening 226 and the cross-section of the bore channel 223 overlap almost totally and the cross-section 232 through which the fluid can move is increased in comparison to FIG. 4. The flow restrictor is almost completely open.

Figure 6:
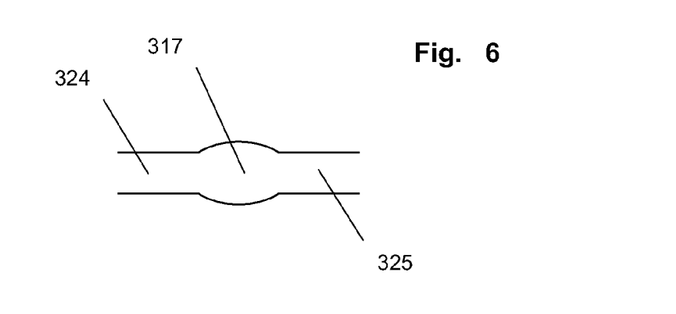
FIG. 6 is a strongly simplified top plan view of a measuring cell.
Figure 7:
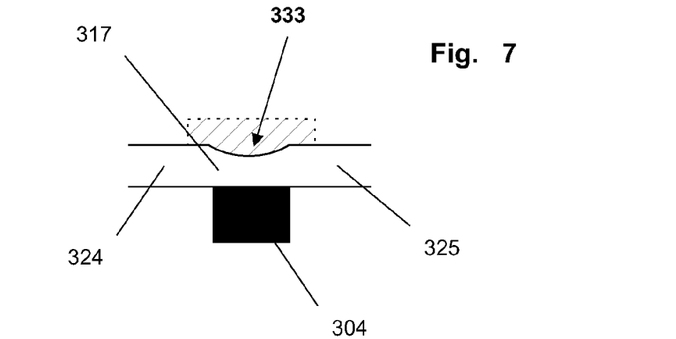
FIG. 7 is a side sectional view of the FIG. 6 measuring cell.

FIGS. 6 and 7, respectively, show top plan and side sectional views of a measuring cell 317 for a sampling device. The taking of samples should take place under the same conditions as are present in the fluid. Included among these conditions is the flow rate. The flow rate through the sampling device and in particular through the measuring cell 317 should remain essentially unchanged. As described hereinabove, the flow rate can be regulated with a suitable adjustable flow restrictor. To ensure in particular that the flow rate through the measuring cell 317 is essentially equal to or smaller than the flow rate in other parts of the sampling device, the measuring cell 317 has a suitably adapted geometry.

The top view of the measuring cell 317 in FIG. 6 shows that the diameter of the measuring cell 317 in this plane is enlarged in comparison to the connector channels 324, 325, which means that the measuring cell 317 has an enlarged base area. The size of the base area is determined, among other factors, by the sensor 304 (see FIG. 7) which works together with the measuring cell 317 and can simultaneously function as a closure element of the measuring cell 317. The measuring cell 317 can also be closed by a suitable, measuring window which is preferably transparent and through which the sensor can measure the sample inside the measuring cell 317.

In order to maintain the flow rate in spite of the enlarged base area, the measuring cell 317 has a reduced profile height in comparison to the connector channels 324, 325 (see also FIG. 7). The wall of the measuring cell comprises an inward-projecting contour shape 333 which is formed in the wall, in a wall element or in the closure element (also see FIG. 9). Due to this design feature, the flow-stream cross-section of the measuring cell 317 is essentially the same as, or smaller than, the cross-section of the connector channels 324, 325 that are connected to the measuring cell 317.

Figure 8:
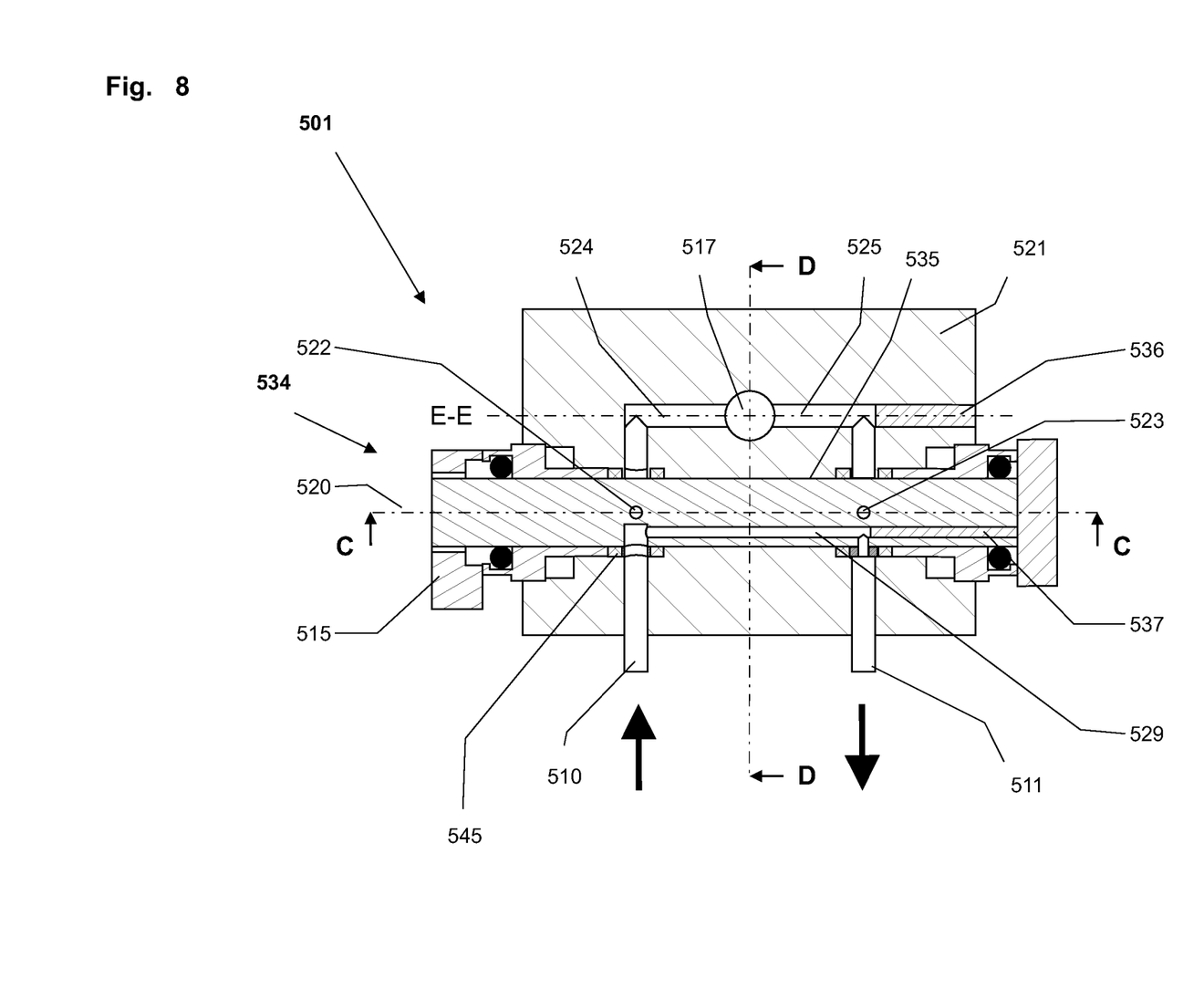
FIG. 8 is a sectional view of a sampling device that incorporates a valve unit, wherein the valve is in the second position.

FIG. 8 shows a sectional view of a further sampling device 501 with an integrally incorporated valve unit 534. The integrally incorporated valve unit 534 and its functions are explained in detail through FIGS. 9 to 17. Obviously, the integrally incorporated valve unit 534 can also be used in instruments other than the sampling device 501.

FIG. 8 illustrates the sampling device 501 with a sampling housing 521, in which a measuring cell 517 connected to first and second connector channels 524, 525, an inlet 510 and an outlet 511 are formed. Also formed in the sampling device 501 is a valve seat 535 which holds the integrally incorporated valve unit 534, allowing it to rotate about its longitudinal axis C-C.

The sampling housing 521 in the illustrated embodiment consists of a transparent material, for example a polymer, so that the sampling device 501 can be inspected visually and/or optically for trapped air bubbles or impurities. Obviously, the sampling housing 521 can also consist of a non-transparent material. The connector channels 524, 525 can be closed to the outside with a suitable closure element 536 as shown here, which can be removed for example for the cleaning of the connector channels 524, 525 and the measuring cell 517.

The integrated valve unit 534 comprises an essentially cylindrical valve body 520 with a first and a second bore channel 522, 523 and a short-circuit channel 529. The two bore channels 522, 523 in the illustrated embodiment are orthogonal to the longitudinal axis C-C and—when the valve is in the second position as shown in FIG. 8—oriented perpendicular to the drawing plane. The longitudinal axes of the bore passages 522, 523 can either be parallel to each other or, preferably, arranged at an angle to each other.

In the second position of the valve, as shown here, the short-circuit channel 529 connects the inlet 510 directly to the outlet 511, so that the inlet can be flushed out with the fluid and trapped air pockets can be pushed out. The short-circuit channel 529 is parallel to, and offset from, the longitudinal axis C-C, so that the short-circuit channel 529 is independent of the bore passages 522, 523. As shown here, the short-circuit channel 529 can extend at least to one end of the valve body 520. If this is the case, the short-circuit channel 529 can be plugged with a further closure element 537. This configuration simplifies the production process and also facilitates the cleaning of the integrated valve unit 534.

The integrated valve unit 534 comprises a first actuator element 515, which serves to move the valve unit 534 between a first position and the second position that is shown in FIG. 8. This change of position is effected by turning the valve body 520 of the integrated valve unit 534 in the valve seat about its axis of rotation C-C. The function of the integrated valve unit 534 as a flow restrictor will hereinafter be explained in more detail.

Figure 9:
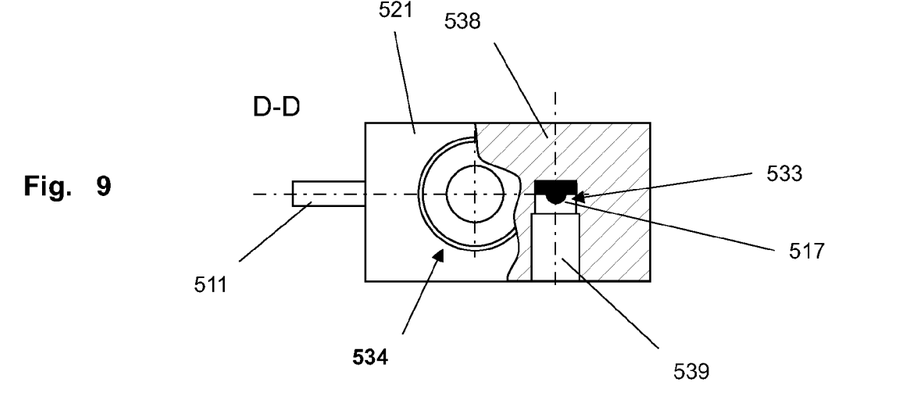
FIG. 9 is an elevation view of the FIG. 8 sampling device, wherein a part of the device is shown in sectional view in the plane D-D.

FIG. 9 shows the sampling device of FIG. 8, wherein the part that contains the measuring cell 517 is represented in sectional view along the plane D-D. The measuring cell 517 is arranged essentially parallel to the longitudinal axis of the integrated valve unit 534 and has a contour shape 533 which serves to equalize the fluid flow through the measuring cell 517, as previously discussed in the context of FIGS. 6 and 7. On the side of the measuring cell 517 opposite the contour shape 533, the sampling housing 521 has a recess 539. By way of this recess 539, a sensor or parts of a sensor can be brought into contact with the measuring cell 517 and/or close off the measuring cell 517. The recess 539 can also be closed with a suitable measuring window.

Figure 10:
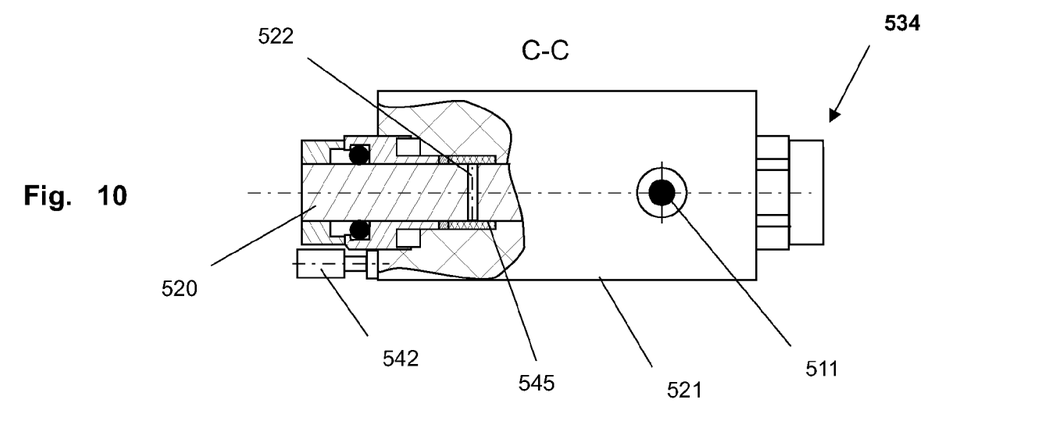
FIG. 10 is an elevation view of the FIG. 8 sampling device, wherein a part of the device is shown in sectional view in the plane C-C.

FIG. 10 shows the sampling device of FIG. 8, represented partially in a sectional view along the plane C-C. The sampling housing 521 is shown with the opening of the outlet 511 facing the viewer. The first bore channel 522 extends through the valve body 520 at a right angle to the axis of rotation C-C of the integrated valve unit 534. The valve has a seal 545 to prevent fluid from penetrating between the valve body 520 and the valve seat 535.

Figure 11:
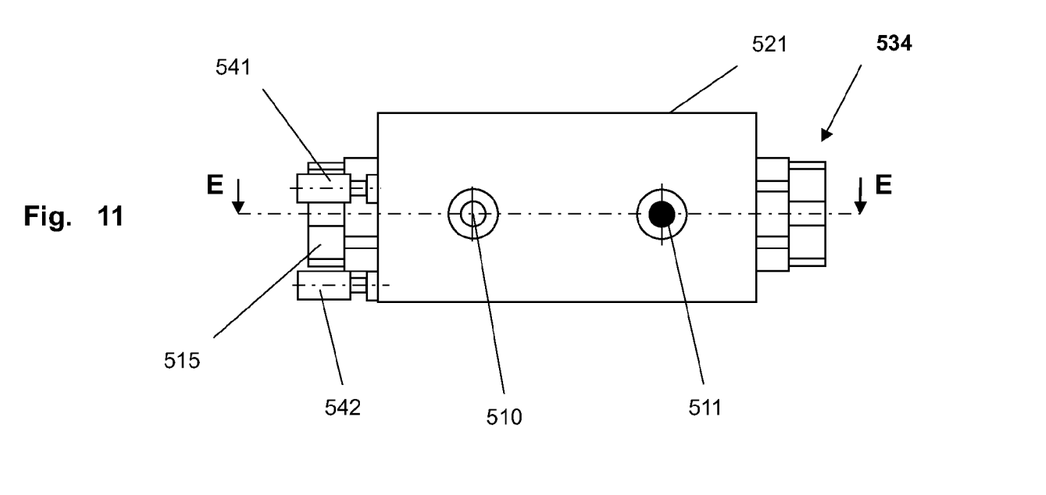
FIG. 11 is a view of the FIG. 8 sampling device seen in the direction of the axis D-D.

FIG. 11 shows the sampling device of FIG. 8 seen from the outside in a view directed parallel to the Axis D-D, wherein a first and a second end stop 541, 542 for the first actuator can be seen.

Figure 12:
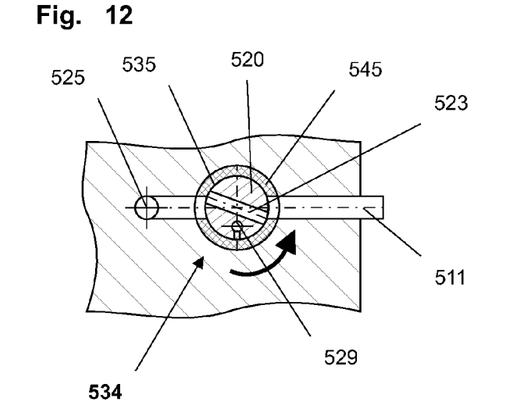
FIG. 12 is a sectional view of the FIG. 8 integrated valve unit in a plane through the outlet, parallel to the axis D-D, wherein the valve is in the first position.
Figure 13:
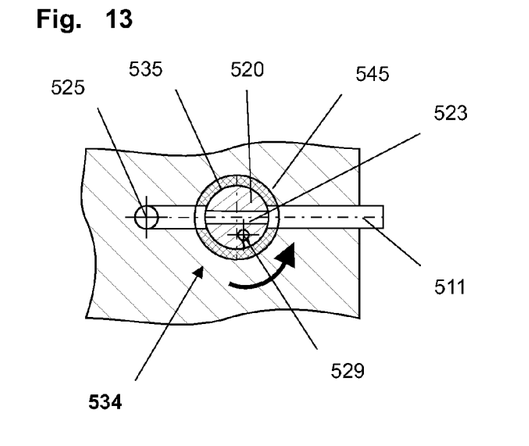
FIG. 13 is a sectional view of the FIG. 8 integrated valve unit in a plane through the outlet, parallel to the axis D-D, wherein the valve is between the first and the second position.
Figure 14:
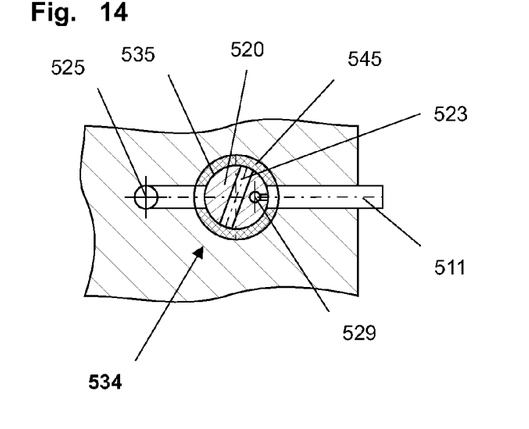
FIG. 14 is a sectional view of the FIG. 8 integrated valve unit of FIG. 8 in a plane through the outlet, parallel to the axis D-D, wherein the valve is in the second position.

Each of FIGS. 12 to 14 shows a sectional view of the integrated valve unit of FIG. 8 in a plane through the outlet and parallel to the axis D-D. The flow restrictor is arranged preferably between the measuring cell and the outlet. Obviously, a flow restrictor can also be arranged between the measuring cell and the inlet, or the sampling device can have more than one flow restrictor.

FIG. 12 shows the integrated valve unit 534 in a first position where the outlet 511 is connected by way of the second bore channel 523 to the second connector channel 525. In the illustrated example, the bore channel 523 has on the one hand a smaller diameter than the connector channel 525, whereby the aperture cross-section of the bore channel 523 is reduced and a fixed-aperture flow restrictor is created. In addition, when the bore channel 523 is in the first position, its axis is set at an angle to the common axis of connector channel 525 and outlet 511, so that the bore channel 523 does not line up completely with the connector channel 525 and the outlet 511. This causes an additional reduction of the flow restrictor aperture, i.e. of the passage aperture cross-section for the fluid. In this position of the valve, the open ends of the short-circuit channel 529 are facing against, and closed off by, the valve seat 535.

When the integrated valve unit 534 is turned in the direction of the arrow shown in FIG. 12, the bore channel 523 is next brought into alignment with the common axis of connector bore 525 and outlet 511, as shown in FIG. 13. In this position, the flow restrictor is set to its maximum passage aperture and the measuring cell is automatically flushed out, so that bubbles and sediments which may be present will be removed.

If the integrated valve unit 534 is turned further in the direction of the arrow, the open ends of the bore channel 523 will face against, and be closed off by, the valve seat 535. At the same time, the short-circuit channel 529 is brought into a position where it intersects the common axis between connector channel 525 and outlet 511, so that the short-circuit channel 529 connects the inlet directly to the outlet (also see FIG. 8). The integrated valve unit 534 is now in the second position, where the measuring cell is disconnected from the inlet and outlet 511 and the inlet can be rinsed out.

Figure 15:
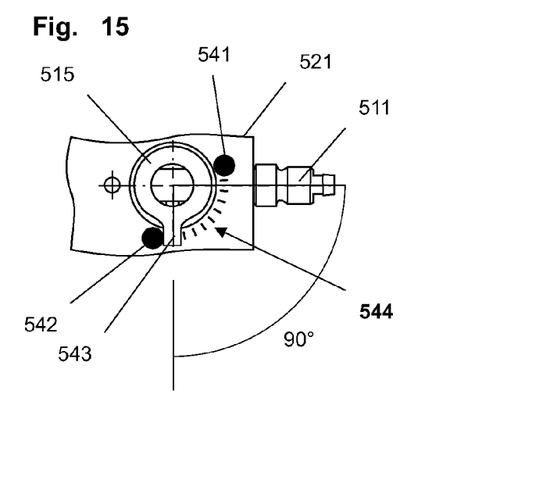
FIG. 15 illustrates the situation of FIG. 12 in an outside view, wherein the valve in the first position.
Figure 16:
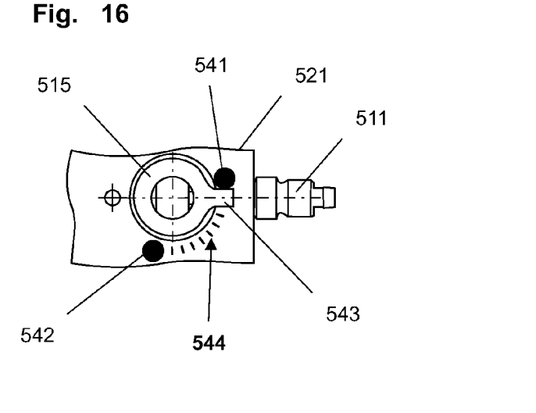
FIG. 16 illustrates the situation of FIG. 14 in an outside view, wherein the valve in the second position.

In this example, the angle of rotation from the first to the second position is about 90°. To enable the user to unambiguously set the first and second valve positions, a first and a second end stop 541, 542 are arranged on the outside of the sampling housing 521 of the sampling device, as shown in FIGS. 11, 15 and 16. The first actuator element 515 has a projection 543 which is moved between the two end stops 541, 542 when the valve body is turned between the first and second positions.

A graduated scale 544 is arranged between the two end stops 541, 542, so that intermediate positions between the two end stops can also be replicated and different aperture widths can thus be set.

In further embodiments, the flow restrictor aperture can be set by varying the distance between the two end stops 541, 542, or the end stops 541, 542 can be arranged on a means of adjustment that is rotatable about the longitudinal axis of the valve body and whose position relative to the bore channels in the valve body can be adjusted and secured. The end stops 541, 542 or the rotatable means of adjustment perform in this case the function of the second actuator element.

In an arrangement were the first and the second bore channel are oriented at an angle relative to each other, the longitudinal axis of the first bore channel is in the first position preferably aligned with the adjoining openings of the inlet and the first connector channel. Only the second bore channel works in this case as a flow restrictor.

Figure 17:
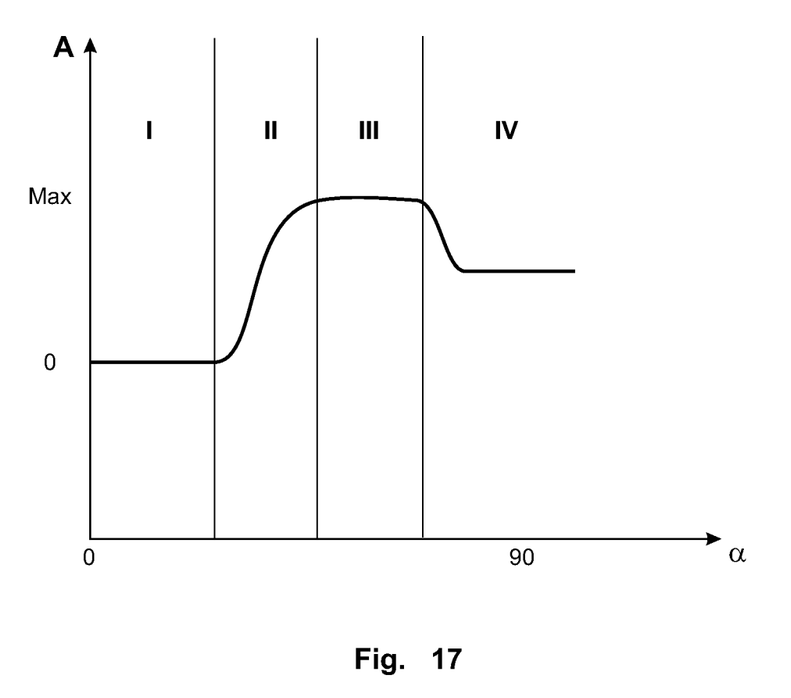
FIG. 17 is a graphical depiction of the flow restrictor aperture in relation to the turning angle of the valve unit.

To illustrate the connection between the angle of rotation α of the first actuator element and the shutter aperture A, the relationship between these two variables is shown schematically in FIG. 17 in the form of a graph of A versus α. At an angle of rotation of α=0, i.e. when the valve is in the second position, the flow restrictor is closed (interval I). The valve is set to the position where the inlet is connected directly to the outlet. From this starting position, the actuator element is turned through its range of 90° to the first valve position. During the turn, the valve is progressively opened (interval II) until the bore channel is oriented parallel to the common axis between the connector channel and the outlet (interval III). In this position, the fluid is directed from the inlet through the measuring cell to the outlet, whereby the measuring cell is flushed out. The flow restrictor is opened to its maximum aperture. As the first actuator element is moved further to the other end stop and thus into the first position, the bore channel is turned partially out of its aligned position between the connector channel and the outlet and the shutter aperture is reduced to the desired width or to a width that is dictated by the end stop.

What is claimed is:

1. A device for taking samples from any one of the following: a pressurized fluid, a fluid containing at least one volatile component and a pressurized fluid containing at least one volatile component, the device comprising:
    a sampling housing;
    an inlet of the sampling housing, through which the sample is received;
    an outlet of the sampling housing, through which the sample is exhausted;
    a measuring cell; and
    a valve unit, comprising:
        a valve which, in a first position, connects the inlet to the outlet by way of the measuring cell and which, in a second position, connects the inlet to the outlet directly while simultaneously disconnecting the measuring cell from the inlet and the outlet; and
        at least one adjustable flow restrictor, comprising a slider with a passage opening, arranged to regulate, within a range that is either continuous or in prescribed steps, the flow of the fluid through the sampling housing.

2. The device of claim 1, wherein:
the valve comprises a valve seat and a substantially cylindrical valve body held in the valve seat, the valve body arranged for rotation about a longitudinal axis thereof by a first actuator element; and
the slider is arranged at least partially inside the valve body for movement along the axis of rotation thereof.

3. The device of claim 2, wherein:
the valve body comprises:
    first and second bore channels that connect the inlet to the outlet through the measuring cell; and
    a short-circuit channel that connects the inlet to the outlet,
wherein the short-circuit channel or the bore channels are offset from the axis of rotation of the valve body.

4. The device of claim 3, wherein:
the short-circuit channel runs non-concentric with, and parallel to, the axis of rotation of the valve body.

5. The device of claim 3, wherein:
at least one of the first and second bore channels intersects the axis of rotation of the valve body.

6. The device of claim 2, wherein:
the valve body, the flow restrictor, the inlet and the outlet are each arranged in the sampling housing; and
the measuring cell, the valve seat, and a first and a second connector channel are each formed in the sampling housing, with each of the connector channels being connected to the measuring cell.

7. The device of claim 6, wherein:
a diameter of at least one of the first and second bore channels in the valve body is smaller than a diameter of the corresponding first or second connector channel to which the bore channel can be connected by rotation of the valve body.

8. The device of claim 2, further comprising:
an elastic element, arranged inside the valve body and abutting an end of the slider that is located inside the valve body.

9. The device of claim 2, wherein:
the valve body and the adjustable flow restrictor form an integrated valve unit, wherein the size of an aperture of the adjustable flow restrictor varies as a function of the angle of rotation of the valve body.

10. The device of claim 2, further comprising:
first and second end stops that delimit the range of rotation of the valve body.

11. The device of claim 1, wherein:
when a dimension used to define a flow-stream cross-section area of the measuring cell increases relative to the corresponding dimension in one of the connector channels, another dimension used to define the measuring cell flow-stream cross-section area is decreased relative to the corresponding dimension in the connector channel, to maintain substantial equality of the respective flow-stream cross-section areas.

12. The device of claim 1, wherein:
the sampling housing is substantially transparent.

13. The device of claim 4, wherein:
when a dimension used to define a flow-stream cross-section area of the measuring cell increases relative to the corresponding dimension in one of the connector channels, another dimension used to define the measuring cell flow-stream cross-section area is decreased relative to the corresponding dimension in the connector channel, to maintain substantial equality of the respective flow-stream cross-section areas.

14. A device for taking samples from any one of the following: a pressurized fluid, a fluid containing at least one volatile component and a pressurized fluid containing at least one volatile component, the device comprising:
    an inlet, through which the sample is received;
    an outlet, through which the sample is exhausted;
    a measuring cell; and
    a valve unit for directing flow of the sample from the inlet to the outlet, the valve unit comprising:
        a valve seat; and
        a substantially cylindrical valve body held therein, the valve body arranged for rotation about a longitudinal axis thereof, such that, in a first rotational position, the valve body connects the inlet to the outlet by way of the measuring cell and, in a second rotational position, the valve unit connects the inlet to the outlet directly while simultaneously disconnecting the measuring cell from the inlet and the outlet; and
    at least one adjustable flow restrictor arranged at least partially in the valve body to regulate the flow of the sample when the valve body is in the first rotational position.

15. The device of claim 14, wherein:
the valve body comprises:
    first and second bore channels that connect the inlet to the outlet through the measuring cell; and
    a short-circuit channel that connects the inlet to the outlet,
wherein the short-circuit channel or the bore channels are offset from the axis of rotation of the valve body.

16. The device of claim 15, wherein:
when a dimension used to define a flow-stream cross-section area of the measuring cell increases relative to the corresponding dimension in one of the connector channels, another dimension used to define the measuring cell flow-stream cross-section area is decreased relative to the corresponding dimension in the connector channel, to maintain substantial equality of the respective flow-stream cross-section areas.

17. An analytical instrument for determining at least one of a chemical and a physical parameter of a sample of any one of the following: a pressurized fluid, a fluid containing at least one volatile component and a pressurized fluid containing at least one volatile component, the analytical instrument comprising:
an analysis housing, having a sensor and a transmitter; and
a sampling device of claim 1, separably connected to the analysis housing, such that the measuring cell of the sampling device cooperates with the sensor when the analysis housing and the sampling device are connected.

18. A method for using a sampling device of claim 1 to take samples of any one of the following: a pressurized fluid, a fluid containing at least one volatile component and a pressurized fluid containing at least one volatile component, the fluid contained in a container, the method comprising the steps of:
connecting the inlet to the container and flushing the inlet and outlet with the fluid by setting the valve unit to the second position;
setting the valve unit to the first position, so that the fluid from the connected container flushes through the measuring cell in the flow path between inlet and outlet; and
taking a sample by either:
with the valve unit in the first position, taking a flow-through sample of the fluid flowing through the measuring cell, or
by switching the valve unit to the second position, a stationary sample is locked into the measuring cell.

\* \* \* \* \*